(12) United States Patent
Stern

(10) Patent No.: US 8,702,636 B2
(45) Date of Patent: Apr. 22, 2014

(54) PODIATRIC SYSTEM

(76) Inventor: Alan M. Stern, Jericho, NY (US)

( * ) Notice: Subject to any disclaimer, the term of this patent is extended or adjusted under 35 U.S.C. 154(b) by 95 days.

(21) Appl. No.: 13/207,878

(22) Filed: Aug. 11, 2011

(65) Prior Publication Data

US 2013/0041304 A1 Feb. 14, 2013

(51) Int. Cl.

| | |
|---|---|
| *A61B 19/00* | (2006.01) |
| *A46B 11/00* | (2006.01) |
| *A47L 13/12* | (2006.01) |
| *A47L 1/08* | (2006.01) |
| *B43K 5/02* | (2006.01) |
| *A46B 11/06* | (2006.01) |
| *A61F 5/00* | (2006.01) |

(52) U.S. Cl.
USPC ............. 602/31; 128/898; 401/16; 401/19; 401/23; 401/24; 401/25; 401/27; 401/40; 401/41; 401/42; 401/43; 401/118; 401/119; 401/126; 401/129; 602/5; 602/23; 602/30

(58) Field of Classification Search
USPC ............. 128/898; 602/30–31; 401/16, 19, 401/23–24, 27, 40–43, 118, 119, 126, 129
See application file for complete search history.

(56) References Cited

U.S. PATENT DOCUMENTS

| | | | | |
|---|---|---|---|---|
| 2,902,146 | A | * | 9/1959 | Doherty .................. 206/361 |
| 5,078,968 | A | * | 1/1992 | Nason ..................... 422/411 |
| 5,181,914 | A | | 1/1993 | Zook |
| 5,869,003 | A | * | 2/1999 | Nason ..................... 422/411 |
| 6,189,539 | B1 | * | 2/2001 | Mitchell .................... 132/73 |
| 6,248,294 | B1 | * | 6/2001 | Nason ..................... 422/411 |
| 6,503,013 | B2 | * | 1/2003 | Strauss .................... 401/123 |
| 7,637,679 | B2 | * | 12/2009 | May et al. ................ 401/133 |
| 2007/0287945 | A1 | | 12/2007 | Cha |
| 2012/0310231 | A1 | * | 12/2012 | Mcerlean et al. ............ 606/33 |

* cited by examiner

*Primary Examiner* — Patricia Bianco
*Assistant Examiner* — Brandon L Jackson
(74) *Attorney, Agent, or Firm* — Gottlieb, Rackman & Reisman, P.C.

(57) ABSTRACT

A device and method for treating an ingrown nail condition is provided. The method prevents a phenol solution that is applied during a P & A procedure from coming into contact with the surrounding skin and nail bed. The device is essentially a plastic tube which comes in different lengths and widths and has a specially shaped aperture located at one end. A stick-shaped cotton applicator is inserted through the tube so as to ensure direct application of the phenol solution onto only the nail matrix. As a result, the phenol solution is prevented from coming into contact with the skin and nail bed, thereby reducing post-operative healing time, post-operative infection and post-operative pain.

3 Claims, 3 Drawing Sheets

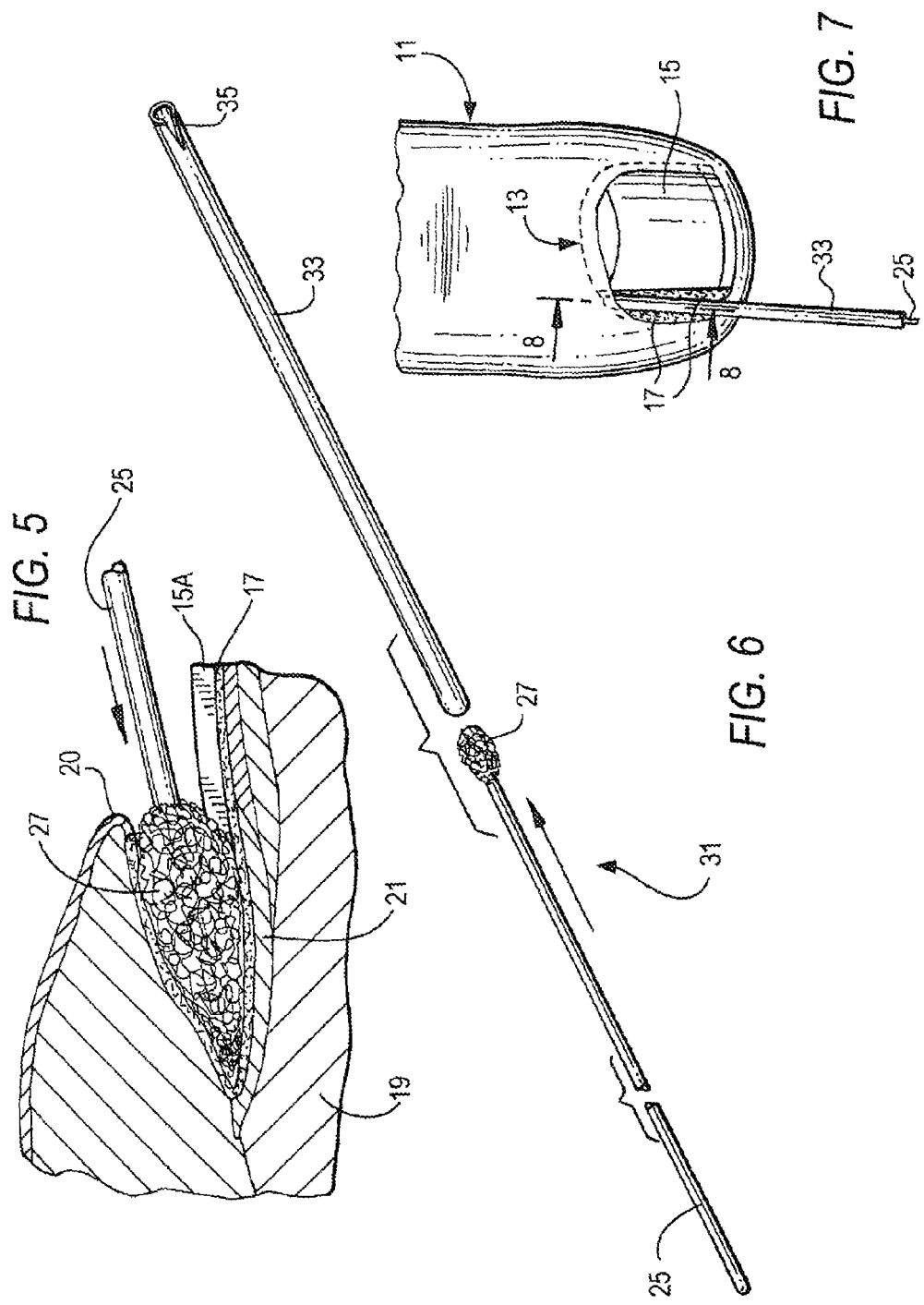

PODIATRIC SYSTEM

BACKGROUND OF THE INVENTION

The condition known as an ingrown toenail is a common form of nail disease. It is an often painful condition in which the nail grows so that it cuts into the side of the nail fold. While ingrown nails can occur in both the nails of the hand and feet, they occur most commonly with the toenails. A true ingrown toenail is caused by the actual penetration of the flesh by a sliver of nail.

The most common cause of an ingrown toenail is cutting one's toenail too short. Other causes can be from wearing socks and shoes that are tight or short. Trauma can also cause ingrown toenails. This includes stubbing your toe or having an object fall on your toenail. Fungal infection of the toenail can also cause an ingrown toenail condition.

Symptoms of an ingrown nail include pain along the margins of the nail, worsening of pain when wearing tight footwear, and sensitivity to pressure of any kind. Indeed, bumping of an affected toe can produce sharp, even excruciating, pain as the tissue is punctured further by the nail. By the very nature of the condition, ingrown nails become easily infected unless special care is taken to treat the condition early on and keep the area clean. Signs of infection include redness and swelling of the area around the nail, drainage of fluid, and watery discharge tinged with blood. The main symptom is swelling at the base of the nail on the side the nail is ingrown.

Ingrown toenails that are left untreated can eventually lead to osteomyelitis, which is an infection in the bone. This serious infection can be especially severe if you have diabetes or circulatory problems in your lower extremities.

Treatment of ingrown toenails depends upon the severity of the condition. Any signs of pain, redness, swelling of the toe or infection should mean a trip to the podiatrist. The doctor may try to recommend simple treatment such as soaking your foot in Epsom salts or in an antibacterial solution. Treatment may also include trimming of the ingrown toenail. However, many times this is only a temporary solution, as ingrown toenails tend to reoccur and become chronic.

A more permanent treatment is to perform what is known as a P & A procedure (phenol and alcohol). This procedure is also called a partial matrixectomy. This procedure eliminates the nail matrix, which is the area from where the ingrown toenail grows. The nail matrix is located behind and underneath the cuticle.

In the P & A procedure, a podiatrist first injects a local anesthetic into the toe to numb it. He next applies a toe tourniquet to prevent bleeding while the procedure is being performed. The ingrown toenail is then removed. The amount of nail that is removed is approximately one millimeter or slightly more. In order to remove the nail matrix, a strong acid such as phenol is used in the procedure.

The procedure comprises inserting a cotton tip applicator into a bottle of phenol and then inserting it under the skin until it comes in contact with the nail matrix. This procedure destroys the matrix area in order to permanently and selectively ablate the matrix that is manufacturing the ingrown portion of the nail (i.e., the nail margin). Thereafter, the area is saturated with an alcohol in order to irrigate the area and for removing any remaining phenol at the surgical site.

In particular, a cotton tip applicator is saturated with phenol. The applicator is then inserted under the skin until it comes into contact with the nail matrix. The applicator is then continuously rotated on the matrix for approximately thirty (30) seconds. The treatment comprises a total of three applications for a combined total of approximately ninety (90) seconds. The surgical site is then irrigated with alcohol to flush out the remaining phenol. A topical antibacterial ointment or cream may thereafter be applied followed by the application of a dry sterile dressing. The toe tourniquet is then removed.

In general, the point of the P & A procedure is to ensure that the nail does not grow back where the matrix has been cauterized/ablated so the chances of further ingrowths are substantially reduced. Occasionally, of course, the ingrown toenail can reoccur which would then require the procedure to be performed again.

The disadvantage to the above described surgical procedure is that the phenol usually also comes into contact with the skin and nail bed, which causes burning and damage to these two soft tissue structures. If this can be eliminated or significantly reduced, the surgical site will heal more quickly. Accordingly, it would be desirable to provide an improved treatment method which overcomes this disadvantage.

SUMMARY OF THE INVENTION

Generally speaking, in accordance with the invention, a device and method for treating an ingrown nail condition is provided. The method prevents a phenol solution that is applied during a P & A procedure from coming into contact with the surrounding skin and nail bed. The device is essentially a plastic tube which comes in different lengths and widths and has a specially shaped aperture located at one end. A stick-shaped cotton applicator is inserted through the tube so as to ensure direct application of the phenol solution onto only the nail matrix. As a result, the phenol solution is prevented from coming into contact with the skin and nail bed, thereby reducing post-operative healing time, post-operative infection and post-operative pain.

As is well known, a phenol solution is a very strong acid. When such a solution comes into contact with the skin and nail bed, it causes burning to both of these soft tissue structures. The inventive tube prevents the phenol solution from coming into contact with the surrounding skin and nail bed by forming an enclosed channel through which the stick-shaped applicator is received. This enclosed channel runs from the tip of the toenail all the way back to the nail matrix during use of the invention.

The inventive applicator is preferably provided with a v-notch at the end of the tube, which enables the phenol solution to come into direct contact with the nail matrix. Thus, when inserting the phenol saturated cotton tip applicator into the inventive applicator or tube, it does not come in contact with the surrounding soft tissue structures. This allows for faster healing time and less risk for post-operative complications.

Accordingly, it is an object of the invention to provide an improved method and system for treating in-grown toenails.

Another object of the invention is to provide a device for preventing the phenol solution that is applied during a P & A procedure from inadvertently coming into contact with surrounding soft tissue structures.

Still a further object of the invention is to provide a method for treating ingrown toenails which promotes healing and reduces post-surgical complications.

Still other objects and advantages will be apparent from the following description.

BRIEF DESCRIPTION OF THE DRAWINGS

Reference is made to the following drawings in which:

FIG. 5 is a cross-sectional view taken along line 6-6 of FIG. 5;

FIG. 6 is an exploded perspective view of the inventive applicator tube along with the cotton tip applicator of the prior art that is to be inserted therewithin;

FIG. 7 is a top plan view illustrating the inventive applicator tube with the cotton tip applicator already inserted therewithin and placed under the skin of the toenail so that there is direct application of the cotton tip onto only the nail matrix;

DETAILED DESCRIPTION OF THE INVENTION

Figure 1:
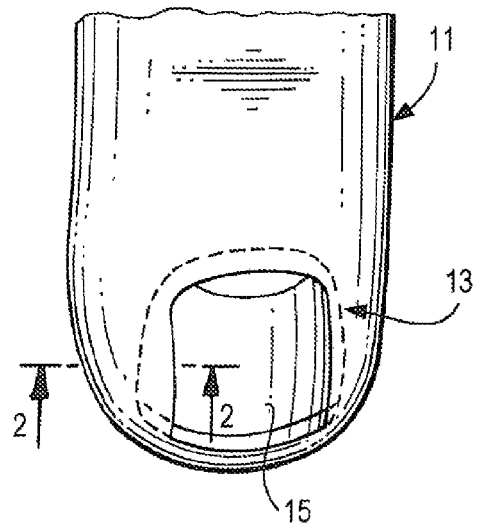
FIG. 1 is a top plan view showing a typical ingrown toenail.
Figure 3:
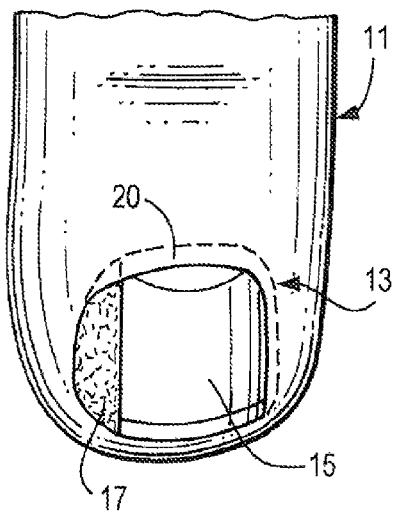
FIG. 3 is a top partial cut-away plan view that is similar to FIG. 1 and which depicts both the nail plate and the nail bed.
Figure 2:
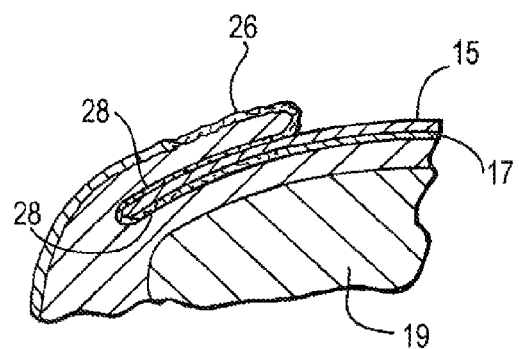
FIG. 2 is a cross-sectional view taken along line 2-2 of FIG. 1.

Referring to FIGS. 1-5, a human toe 11 of a conventional type is shown. Toe 11 leads to a distal end that defines a toenail generally indicated at 13. Nail 13 includes a nail plate 15, which is the actual nail member, the nail matrix 21, which is the tissue upon which the nail rests and which extends beneath the nail root, and the nail bed 17, which is the skin beneath nail plate 15. Below the nail matrix 21 is bone 19 of toe 11 and nail cuticle or nail fold 20 is the thickened layer of skin surrounding nail 13.

Figure 4:
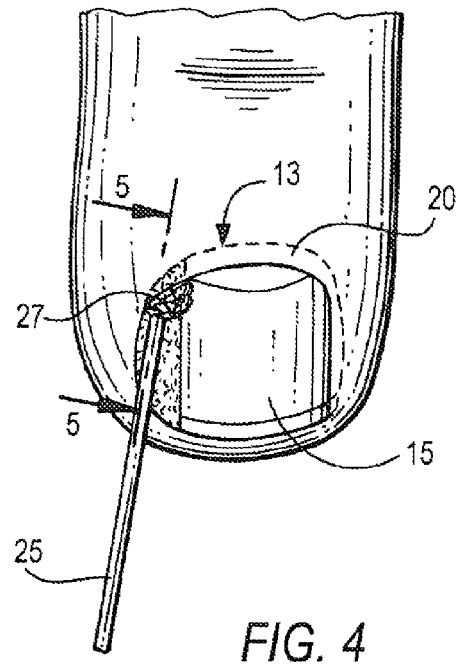
FIG. 4 is a top plan view illustrating the placement of a cotton tip applicator under the cuticle and skin of the toenail in accordance with the prior art until it comes in contact with the nail matrix.

As shown best in FIG. 4, an ingrown toenail condition is depicted in which toe skin 26 is overgrown around the nail plate 15. As a result, nail plate 15 penetrates the flesh surrounding nail 13, causing infection in tissue region 28 in which nail plate 15 is buried. As described hereinbefore, and as illustrated in FIGS. 4 and 5, there is a well-known surgical procedure for treating the condition of an in-grown toenail known as a P & A procedure. Prior to carrying out the P & A procedure, the ingrown portion of nail plate 15 is first cut away or otherwise removed (see FIG. 3), leaving behind a remaining portion 15A of the nail plate (see FIG. 5).

A P & A procedure uses a stick-shaped applicator 25 made from wood and having a cotton moisture absorbing tip 27. Tip 27 of applicator 25 is inserted into a phenol or other acid solution so that tip 27 absorbs some of the solution. Following removal of the ingrown portion of nail plate 15, tip 27 of applicator 25 is then inserted under nail fold 20, as best shown in FIG. 5, such that tip 27 can come into contact with nail matrix 21. By doing so, the portion of matrix 21 that was producing the ingrown portion of nail plate 15 is able to be ablated and thereby destroyed. However, the problem with carrying out this procedure, as previously described, is that the phenol solution that is absorbed onto tip 27 of applicator 25 will frequently come into contact with the skin and with nail bed 17, which causes burning and damage to those soft tissue areas, thereby slowing down the subsequent healing process.

Figure 8:
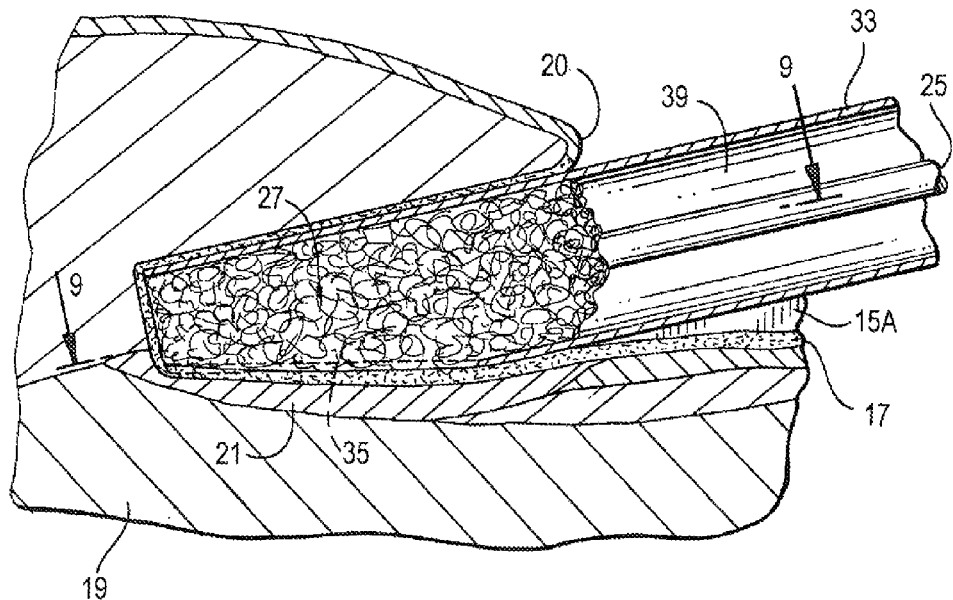
FIG. 8 is a cross-sectional view taken along line 8-8 of FIG. 7.
Figure 9:
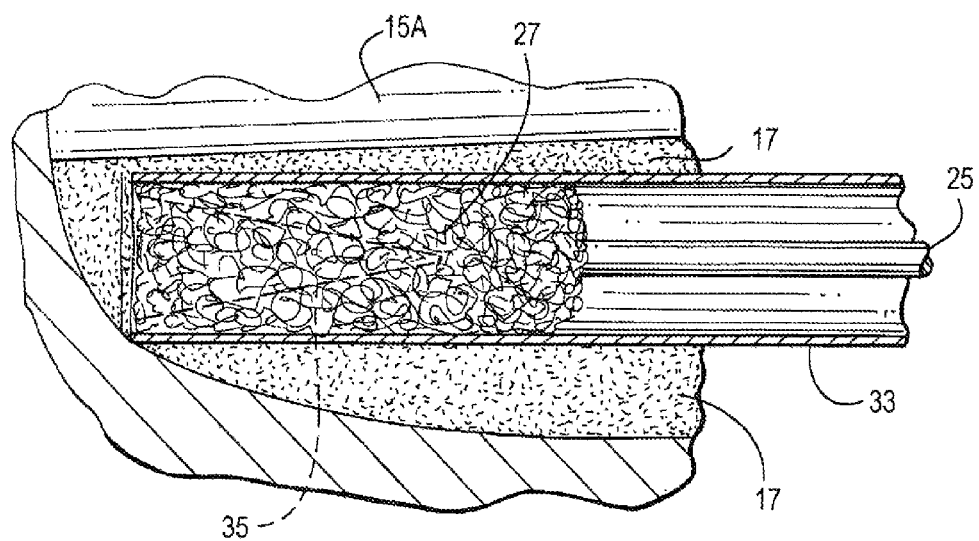
FIG. 9 is a cross-sectional view taken along FIG. 9-9 of FIG. 8.

In accordance with the invention, as best shown in FIG. 6, an applicator unit 31 is designed that includes an applicator tube 33 in combination with stick applicator 25. Applicator tube 33 is typically made of plastic and is designed to be produced in different lengths as needed. Tube 33 includes a V-cut aperture 35 at one end and is sized to selectively receive applicator 25 therewithin. More particularly, tube 33 has a channel 39 formed therethrough which can selectively receive applicator 25, as shown in FIGS. 7-9.

In operation, applicator 25 is inserted into tube 33 such that tip 27 is disposed where V-cut aperture 35 is formed. Thereafter, applicator unit 31 is inserted under nail fold 20 such that the end of tube 33 where aperture 35 is formed and where tip 27 of applicator 25 is located contacts nail matrix 21. Because of the overall construction of applicator unit 31, the phenol solution that is carried by applicator tip 27 is prevented from contacting surrounding skin as well as nail bed 17 since tube 33 forms an enclosure to applicator 25. Moreover, aperture 35, formed at the end of tube 33, allows the phenol solution that is carried on tip 27 of applicator 25 to come into direct contact with nail matrix 21, but still prevents it from contacting surrounding soft tissue structures.

After applying the phenol solution carried by applicator tip 27 to nail matrix 21, alcohol is applied to nail bed 17 for irrigation purposes in order to remove the phenol solution.

The scope of the invention will now be set forth in the following claims.

The invention claimed is:

1. A method for treating an ingrown condition of a nail, the nail including a nail plate, nail matrix and nail fold, the method comprising the steps of:
   removing an ingrown part of the nail plate;
   determining a portion of the nail matrix from which an ingrown part or the nail plate was being manufactured;
   ablating said nail matrix portion by contacting said nail matrix portion with an acid solution;
   wherein said ablating step includes the steps of applying said acid solution to one end of a stick-shaped applicator, sliding said stick-shaped applicator through a tube having a first open end through which said applicator end is first inserted and a second open end, disposing said tube with the applicator underneath said nail fold, exposing said end of said stick shaped applicator through said second end of said tube, and contacting said nail matrix portion of said nail with said one end of said applicator in order to apply said acid solution only onto the nail matrix.

2. The method of claim 1, wherein said method further includes the step of irrigating said nail in order to remove said applied acid solution.

3. The method of claim 1, further including the step of forming an aperture or cut-out at said one end of said tube to facilitate exposure of one end of said applicator.

* * * * *